GRAPEVINE

Filed May 14, 1973 2 Sheets-Sheet 1

United States Patent Office

Plant Pat. 3,625
Patented Sept. 24, 1974

3,625
GRAPEVINE

Harold P. Olmo, Davis, Calif., assignor to The Regents of the University of California, Berkeley, Calif.

Filed May 14, 1973, Ser. No. 360,269
Int. Cl. A01h 5/03
U.S. Cl. Plt.—47 1 Claim This invention relates to a new and distinct variety of grapevine of the vinifera species to be used primarily for the production of red table wine.

According to the variety census of 1971, the principal varieties grown in the San Joaquin Valley of California for red table wine are Carignane (20,934 acres) and Grenache (11,246 acres).

Carignane remains the predominant variety in the San Joaquin Valley, not because winemakers consider the variety satisfactory, but because growers are reluctant to part with an old friend that is a consistent and heavy producer of sound fruit, and a vine that is easily trained and handled. It is a variety that has inherent difficulty in reaching optimum sugar content and can be overcropped too easily. It is widely adapted to all climatic areas expcept the coolest coastal zones where it fails to ripen. The wine retains some bitterness and the color in most seasons is too light and tends to oxidize. The wine has no characteristic aroma or flavor that allows recognition and, hence is classed as a common or blending variety.

The Grenache occupies second place. It is a very rugged, long-lived and resistant vine and under proper condition gives high yields of well ripened fruit. Unlike the Carignane, it is very sensitive to cool and damp climatic conditions, both at blossom time and at fruit maturity. Yields in the cooler and heavier irrigated soils are very erratic and botrytis rot of the maturing fruit after a fall rain can be disastrous. It is at its best on deep sandy or gravelly soils that dry out easily and in arid zones where late rains before harvest time are at a minimum. The wine has a distinctive and strong flavor, but the color is always deficient and the wine oxidizes easily to orange and then browns.

The objective in producing this new variety was to retain the desirable viticultural features of the Grenache and Carignane, especially high yield and good cultural characteristics, but to improve the wine quality. The improvement in wine quality is largely obtained from the Cabernet-Sauvignon parent, which contributes a more stable red color and more flavor and aroma.

The original cross in 1936 between Carignane x Cabernet-Sauvigon that produced the Ruby Cabernet also produced a very vigorous vine that bore fruit of Cabernet flavor and gave a high scoring wine, yet of light body and rapid maturity. This selection, F2–7, was unproductive because it had female flowers. Nonetheless, it was used for further crosses. The F2–7 was crossed with a Grenache in 1949 from which was selected the new variety 12. The new variety was then successfully asexually reproduced by budding it onto older vines and the reproductions carry forward all of the novel characteristics of the new variety. The new variety was first fruited in 1954 in The University of California vineyard at Davis, Calif.

After preliminary tests at Davis, Calif., it was propagated in larger lots in trial blocks at Lodi, Calif., in 1961, Modesto, Calif., in 1961, Madera, Calif., in 1966, and at Fresno, Calif., in 1967. When the vines came into bearing, 100 pounds of grapes were harvested and brought to Davis, Calif. where a five gallon lot of wine was produced.

*The Vine:* The vine is vigorous, upright in habit with a very straight trunk of moderate diameter, and is consistent in its bearing habit, having few canes and a minimum of branching. It is easily trained and pruned and when mature it resembles the Grenache more than any other standard variety, but is less vigorous. Buds in the old wood are fruitful so some crop recovery after spring frost is possible. The leaf canopy is good and affords protection from sunscald of the fruit.

*Shoot Tip:* Shoot tip (10″–12″) moderately recurved, tomentum light cream colored; only margins of youngest leaves are pink, unfolding leaves soon becoming arachnoid hairy above and below; newly expanded leaves have smooth surface, light yellow-green, very glossy.

Figure 1:
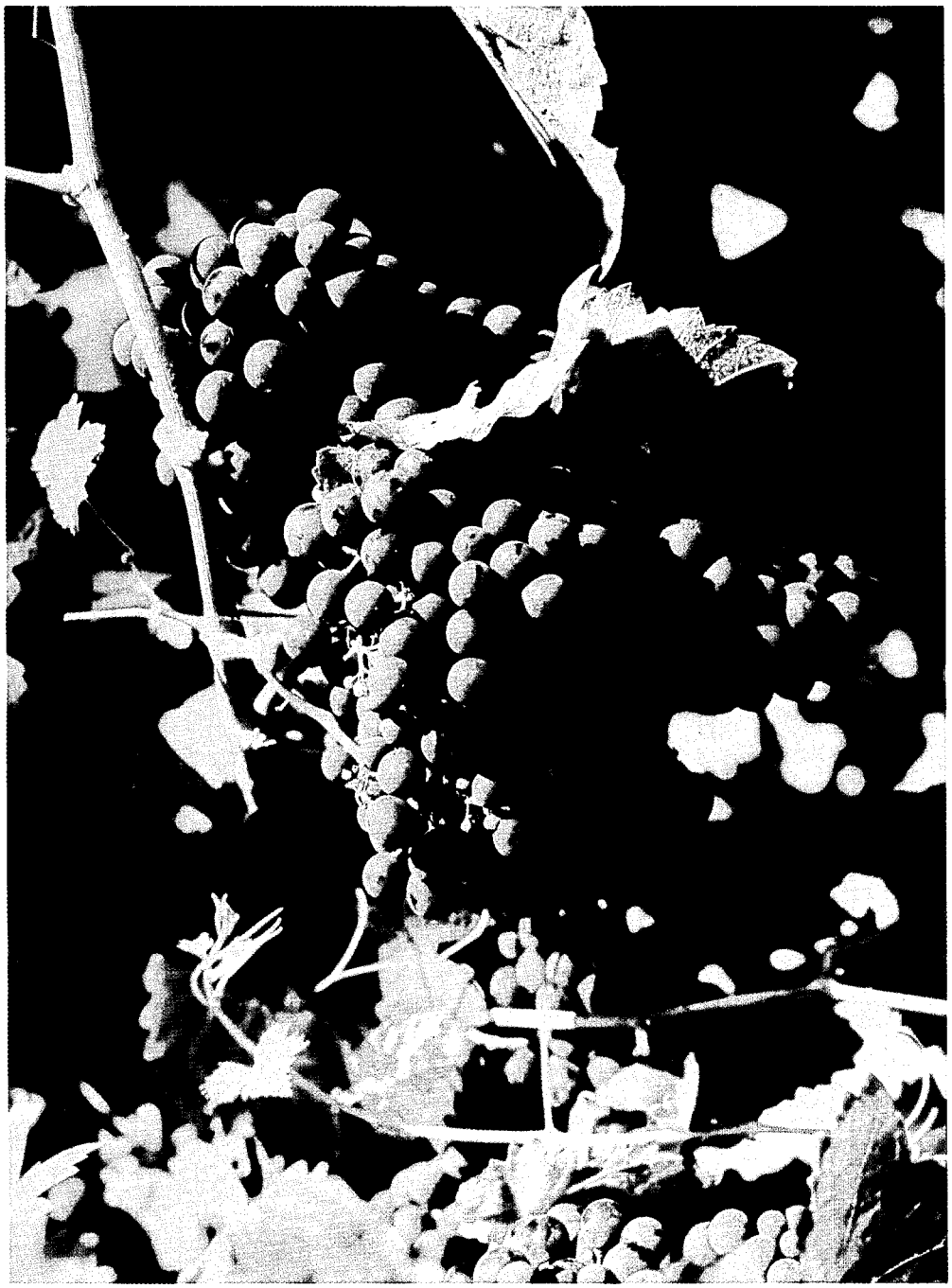
FIG. 1 is a view of a typical cluster and stem of the new variety.
Figure 2:
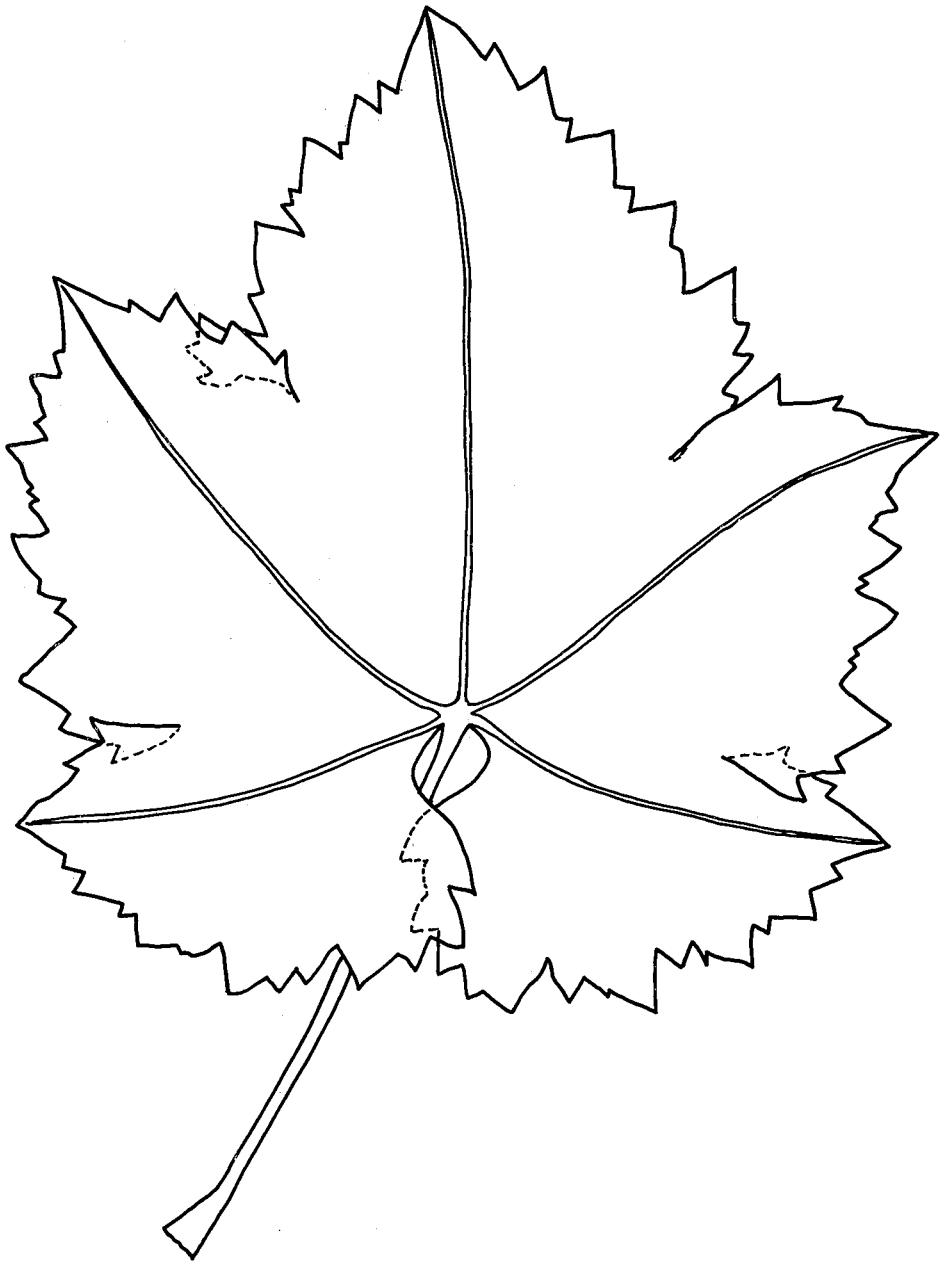
FIG. 2 illustrates in outline form a typical leaf of the new variety.

*Leaf:* The mature leaf with the blade almost as wide as long, 17 cm. x 18 cm. is three-lobed and completely glabrous above and below; the principal veins on the underside are whitish and prominent. The upper sinuses are deep, but completely closed by the widely overlapping lateral lobes caused by the incurving lateral veins. The lower sinuses, when present, are reduced to small narrow slits. The petiolar sinus is lyre-shaped, of medium width and is partly closed by the overlapping basal lobes. An outline drawing of a typical leaf is shown in FIG. 2. The marginal teeth are large on the upper lobes, usually in a single series, with apices forming an equilateral triangle.

*The Canes:* The canes are of medium length, round in cross section, very straight and few in number, thus easily pruned. The color is light brown with faint striations of darker brown. The nodal regions are in sharp contrast with darker brown color. The eyes are small, elliptical, pointed and firmly sealed with the bud scales. The secondary branches are very short and weak, and hence the second clusterlets are usually absent.

*The Cluster:* The cluster is compact or very compact as the flower set is excellent in all of the regions of the San Joaquin Valley where the variety has been tried, yet spoilage has not been a serious problem. The primary cluster averages 455 gm. (range 250–817), short conical (10.6 cm. x 16.6 cm.) in shape. It is seldom winged. An unusual and good identifying characteristic is the almost equal size of the primary and secondary clusters on the same cane and they often touch because of the short internode length between them. This has some advantage in mechanical harvest as it concentrates the fruit in a narrower band on the trellis. Weak canes may bend to a pendant position from the weight of the fruit unless supported.

The cluster stem is thick, averaging 4 mm. in diameter at the base, and usually remains green and unlignified except at the juncture to the cane. The stem structure makes up 2.1% of the cluster weight on a fresh basis. The mean number of berries per primary cluster is 185. The berry is slightly ellipsoidal to spherical in shape, the skin is thick, blue-black in color, with heavy bloom and is slow to lose moisture or shrivel. The pedicels are thin, 6 mm. in length, with a thin but widely flanged torus. The adherence of the berry is good. No heat damage or sunscald has been observed over a ten-year period. The single berry weight (sample of the ten largest per cluster) is 2.5 gm., compared with Carignane at 2.2 gm. The seed is very small, 100=2.207 g. air-dried; the beak is knobbed and yellowish, folds light brown, and vascular remnant at micropyle drying to a conspicuous purple-black projection. The seed distribution per berry is 3–36–50–11, as percentage of berries with 1, 2, 3 and 4 seeds. Seedless berries are absent.

Berry skin and flesh color is that of Cabernet-Sauvignon, and flesh texture is that of Carignane.

The fruit is ready for commercial harvest in the Central Valley of California from the middle to the end of September. At this stage the sugar content is relatively low, from 20° to 21° Balling. The total acidity remains higher than Carignane or Grenache, and is optimum when in the range 8.0 gms. to 9.0 gms. per liter, as tartaric acid. The pH of the fresh juice is lower than most varieties, often being in the 3.20 to 3.30 range. This is considered a very desirable factor in the stability and conservation of the wine. The wine has the property of becoming drinkable at an early age.

*The Variety:* The distinctive features of the variety are its heavy yield of sound fruit from which can be produced a medium red table wine of good quality when grown in the hotter grape growing regions of the Central Valley. The wine is characterized by having medium body, excellent red color and pleasing flavor; retaining an unusually high acidity and low pH for such warm growing regions. Rose wines of light red or pink color are also of fine quality. The variety can be used for the production of port type wines in some areas. These conclusions are drawn from wine making tests made during the period 1966 to 1971 from fruit harvested near Ceres (Modesto), Calif., and in 1970 to 1971 from plots near Lodi and Fresno, Calif. The wine matures quickly and can be consumed young, but will also improve on aging. The quality is superior to the Carignane and Grenache, now the most widely grown varieties for red table wines in the Central Valley. This is reflected in deeper red color, finer flavor and a higher acid content.

I claim:

1. The new and distinct variety of grapevine herein described and illustrated, and identified by the characteristics enumerated above.

No references cited.

ROBERT E. BAGWILL, Primary Examiner